United States Patent [19]
Karami et al.

[11] Patent Number: 4,726,976
[45] Date of Patent: Feb. 23, 1988

[54] COMPOSITE SUBSTRATE

[75] Inventors: Hamzeh Karami, Weston; David J. Korn, Melrose, both of Mass.

[73] Assignee: The Kendall Company, Boston, Mass.

[21] Appl. No.: 923,930

[22] Filed: Oct. 28, 1986

[51] Int. Cl.[4] .......................... B32B 3/10; B32B 7/10; B32B 31/20
[52] U.S. Cl. .................................... 428/137; 156/176; 156/253; 156/290; 156/308.4; 156/309.6; 428/138; 428/198; 428/286; 428/287; 428/339; 604/366
[58] Field of Search ............ 156/176, 253, 290, 308.4, 156/309.6; 428/137, 138, 198, 286, 287, 339; 604/366

[56] References Cited

U.S. PATENT DOCUMENTS 3,292,619 12/1966 Egler .
3,331,728 7/1967 Lane .
3,622,422 11/1971 Newman .
3,660,200 5/1972 Anderson .
3,676,242 7/1972 Prentice .
4,115,176 9/1978 Ekstrand .
4,379,192 4/1983 Wahlquist et al. .
4,522,203 6/1985 Mays .

FOREIGN PATENT DOCUMENTS 1185227 3/1970 United Kingdom .

Primary Examiner—James C. Cannon
Attorney, Agent, or Firm—Francis J. Clark

[57] ABSTRACT

A composite substrate for use as a coversheet on disposable articles such as disposable diapers, sanitary napkins, disposable bed pads, nursing pads, finger dressings, and incontinent diapers, or the like. The cover sheet comprises an inner layer of polyethylene thermoplastic film secured to and between the inner surfaces of a top layer and a bottom layer of nonwoven polypropylene fibrous webs, by means of a pair of, one of which being a heated embossed roll applied to at least one of the outer surfaces of the fibrous web. The heat from the heated roll causes the film to melt in discrete areas forming apertures therein without substantially affecting the fibrous webs. As the film melts, it contacts fibers in the substantially unaffected adjacent fibrous web layers, causing the film and webs to be secured to each other at least at the peripheral edges of the discrete apertured areas, leaving a matrix of fibers covering the apertured areas.

11 Claims, 5 Drawing Figures

COMPOSITE SUBSTRATE

BACKGROUND OF THE INVENTION

1. Field of Invention

This invention relates generally to coversheets for such absorptive devices as disposable diapers, sanitary napkins, disposable bed pads, nursing pads, finger dressings, and incontinent briefs, or the like.

2. Prior Art

Usually, absorptive devices consist of a coversheet, an absorbent pad and a barrier sheet in close contact with each other.

Prior art coversheets usually consist of a flexible apertured plastic sheet to prevent liquid absorbed in an absorbent pad, within an absorptive device, from striking through and soiling outer adjacent clothing. The apertured waterproof plastic sheet of the prior art does provide some degree of dryness. In order for an absorptive device to be acceptable to the public, specifically women, liquid excreted by the body must be capable of being transferred through the coversheet, which is in intimate contact with the body, away from the body into an absorbent pad as quickly as possible. Thus, this quick transmittal of liquid through a coversheet is an essential requirement in developing an absorptive device. In addition, the prior art plastic sheets do not adhere or come into intimate contact with an absorbent pad. Thus, this may result in the absorbent pad shifting within the device thereby causing problems. Additionally the prior art plastic sheet material has an undesirable touch and it sticks to the skin of the user. The present invention has a textile-like surface which results in excellent comfort when in contact with the skin.

In U.S. Pat. No. 3,881,489, there is provided a disposable absorptive device having an absorptive body enclosed within a top coversheet and an improved breathable liquid impervious backsheet. The topsheet may be any conventional top sheet, such as described in U.S. Pat. Reissue No. 26,151. The improved backsheet comprises the combination of two distinct adjacent hydrophobic layers to form an effective breathing portion of the backsheet. The first layer being liquid permeable and having a low void volume while the second layer is liquid permeable and having a higher void volume than the first. The combination of the two backsheet layers prevent the passage of liquid while permitting the passage of gase therethrough. A disadvantage associated with the aforementioned prior art is that the topsheet is a typical topsheet made from a plastic film without any distinguishing features, such as dryness or fluid penetration.

In U.S. Pat. No. 3,292,619, there is described an invention directed to a non-adherent dressing in which only portions of the surface of the body side thereof are in contact with the body when applied to cover a wound therein. Only a minor portion of the total surface area of the body side of the dressing is in contact with the body. The major sites of fluid intake into the absorbent pad, in accordance with that invention, are located in depressions in the surface of the dressing which is in contact with the body. The walls of the depression are sloped inwardly into the body of the dressing and are lined with a thin film which covers the surface of the pad at the body side of the dressing. The film lining the walls of the depressions is perforated. Each depressed film portion containing a plurality of openings into which the fluid passes. A disadvantage of this prior art fabric is that it is bonded together by passing it between the nip of an embossed roll and a smooth surface roll which imparts depressions to the fabric. The depressions in the fabric thus reduce the total area that is available in the absorbent material for absorbing fluid.

In U.S. Pat. No. 3,331,728, there is described a film-fiber laminate that is made as a coversheet to cover absorbent material, such as that used in a sanitary napkin. The laminate is made in a continuous process with the film, as formed by a film extruder, being laid immediately onto an underlying perforated fiber web. Suction is then applied to the underside of the perforated web, with the freshly extruded film still in the highly tacky fluid state, to secure intimate bonding between the film and the underlying fibrous web, while at the same time rupturing the film in the areas immediately overlaying the openings in the fiber web, causing openings to be completely through the fabric. A disadvantage of the aforementioned prior art is that the openings in the composite are through the film and the fibrous web. This allows for ingress of fluid to pass through the composite into an absorbent material, but also allows for egress of the fluid, thus presenting a problem in containing fluid in a product, such as a sanitary napkin.

The aforementioned disadvantages in the prior art are not present in this invention because it is an integral composite made in one process step, having no depressions and no holes through the fibrous web. In addition to it being more economical to produce, it has qualities that are not present in the prior art which will be more evident in the remainder of this specification, drawings and claims.

An object of this invention is to provide a substrate having excellent tensile strengths, fluid penetration rewet properties, and textile-like surfaces.

Another object of this invention is to provide a coversheet having minimal fluid retention capacity.

Still another object of this invention is to provide a coversheet that has a fibrous surface on one side that will contact the wearer skin to give comfort and on the opposite side a fibrous surface that has sufficient roughness to stay in intimate contact with an absorbent material adjacent thereto.

SUMMARY OF THE INVENTION

A composite substrate to be used as a composite on disposable articles, comprising at least one middle layer of a polyethylene thermoplastic film that is secured to the inner surfaces of at least a top layer and a bottom layer of nonwoven polypropylene fibrous webs when a heated embossed roll, having lands and grooves, is applied to at least one outer surface of one of the fibrous webs. The heated lands of the roll causes the film to melt in discrete areas forming apertures only in the film, while not substantially affecting the fibrous webs. As the film melts, it contacts the adjacent fibrous web layers in discrete areas, causing the film and webs to be secured to each other at least at the peripheral edges of the discretely apertured areas. Because the fibrous webs are substantially unaffected, a matrix of fibers remains on each side of the substrate covering the apertures.

BRIEF DESCRIPTION OF THE DRAWING

The objects and advantages of the present invention will become apparent when viewed in conjunction with the following drawings, in which.

DESCRIPTION OF THE PREFERRED EMBODIMENT

The goal of prior art has been to develop a composite substrate having excellent tensiles; minimal fluid holding capacity; fluid penetration and rewet properties for use as a coversheet on disposable articles, such as diapers and sanitary napkins.

To achieve most of these goals the prior art has used separate layers to make up a disposable article. These layers usually consist of a layer of plastic film as a coversheet and a layer of absorbent material encased in said coversheet. When substrates are used as a coversheet on a sanitary napkin, the top surface must not hold any of the menstrual fluid and must have minimal stain in order to be well accepted by women. Another requirement is that the substrate have a side with a comfortable surface and another side with a surface having enough roughness to stay in intimate contact with an absorbent pad in a sanitary napkin. This surface roughness is to hold the absorbent pad in place thus facilitating the transmission of fluid from an apertured substrate into the absorbent pad.

The fibers are compressed into the aperture as melting of the film occurs thus creating a matrix of fiber melted film within the aperture.

This fluid will pass through the coversheet into the inner absorbent pad but because fibers cover the apertures in the coversheet, they form a barrier so as to restrict fluid from exiting back out through the coversheet.

The present invention has achieved what the prior art has been unable to do by providing a composite having a fiber-film-fiber structure with the aforementioned properties. In addition to hygienic products, this invention may be used, as a substrate for a tape backing, tea bags, filtration membranes, wipes, sponges, finger dressings, milk filters or filters for wine, beer, oil etc.

Figure 1:
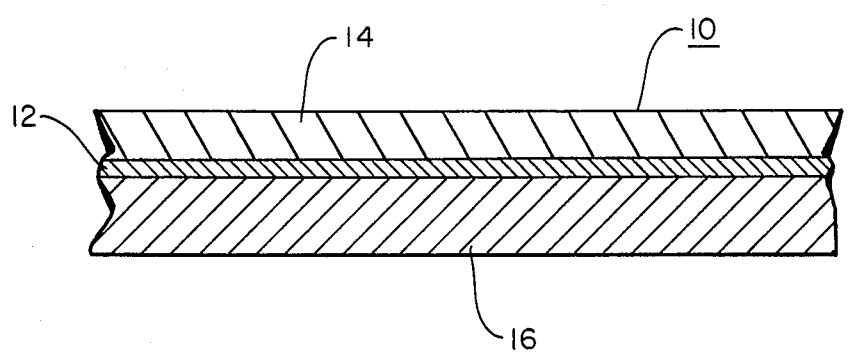
FIG. 1 is a cross-esctional view of the composite substrate illustrating the layers of said substrate.

The present invention substrate 10, as shown in FIG. 1, may be made of an inner layer of polyethylene thermoplastic film 12 between and secured to the inner surfaces of at least one top 14 layer and one bottom 16 layer of nonwoven polypropylene fibrous webs. Although the aforementioned construction is the preferred embodiment, the film layer may also be made from any thermoplastic film, such as polypropylene, polyurethane, polyester, co-polyester or co-polypropylene. The top and bottom fibrous layers 14 and 16, may be made from any synthetic fiber, such as polyolefin, rayon, polyester, or acrylic, or natural fibers, such as cotton, wood pulp, or any combination of synthetic and natural fibers. In addition, the nonwoven fibrous web could be made of staple fibers, continuous filaments or microfibers.

Additionally, the top layer of fibrous web may be made of hydrophobic fiber, while the bottom layer of fibrous web may be made from hydrophilic fiber. Although the aforementioned is the preferred embodiment of the present invention, a blend of hydrophobic and hydrophilic fibers may also be used as long as the bottom layer has substantially more hydrophilic fibers. For example: The top layer may have at least 1% hydrophilic fibers, while the bottom layer may have at least 5% hydrophobic fibers.

Figure 2:
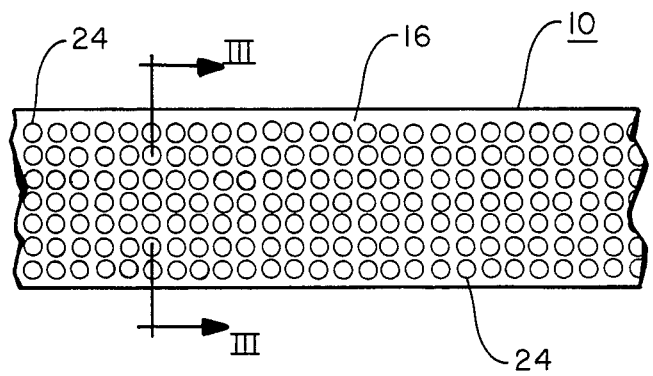
FIG. 2 is a view of the composite substrate to illustrate the apertures within the film.
Figure 3:
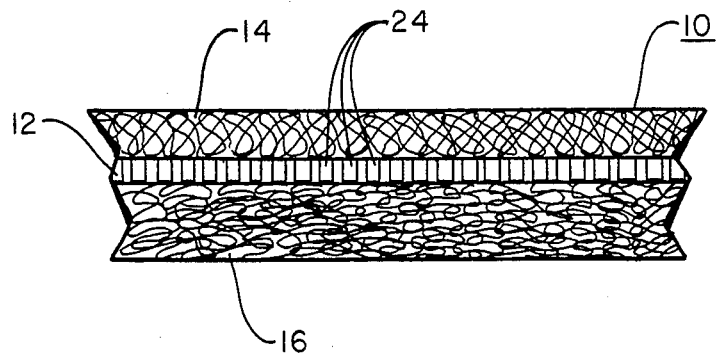
FIG. 3 is a cross-sectional view taken along the lines III—III of FIG. 2 to illustrate that the apertures do not penetrate through the fibrous webs.
Figure 3A:
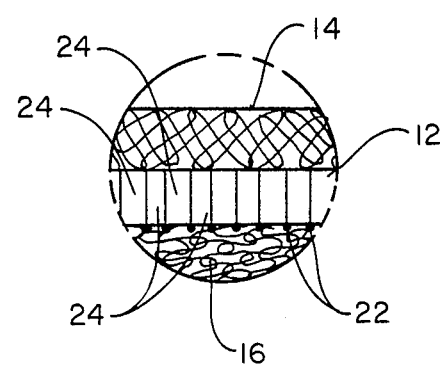
Figure 4:
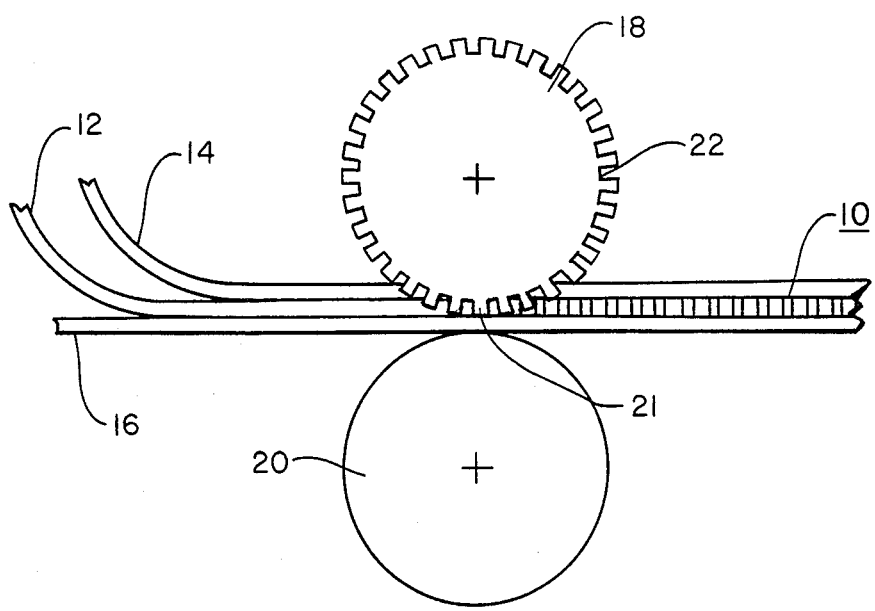
FIG. 4 shows the film and the fibrous webs as they are passed between a heated embossed roll and a smooth roll.

As shown in FIG. 4, the film layer 12 is positioned between the top hydrophobic layer 14 and the bottom hydrophilic layer 16 of the fibrous web. The film layer 12 and fibrous web layers 14 and 16 are then fed between two mechanically driven heated rolls, 18 and 20. The top roll being an embossed roll 18, having a peripheral array of lands 21 and grooves 22, and the bottom roll being a smooth roll 20. The smooth roll 20 may be cooled by known means to maintain a constant temperature. The embossed roll 18 may have varying patterns on its surface, depending on the aperture requirements. The embossed roll 18 is set at a position whereby the raised lands 21 of the roll 18 barely makes contact with the surface of the top hydrophobic layer 14, as shown in FIG. 4. As the heated lands 21 of the roll 18 contacts the surface of the fibrous web, the heat radiating from the surface of the lands 21 melts the film in discrete areas. As the film melts in these discrete areas, apertures 24 are created or formed in the film 12, as shown in FIG. 2. In addition, as the melted film 22 flows, it contacts fibers in the fibrous layers, as shown in FIG. 3A. Then, as the composite layered substrate 10 exits the nip of the pair of heated rolls 18 and 20, the melted film cools and the layers become secured to each other in the discrete areas of the apertures 24, also shown in FIG. 3A, at least at the peripheral edges of those apertured areas. It is important to note that the heated lands 21 of roll 18 do not substantially affect the structure or composition of the fibrous layers in any manner because the fibers in the fibrous layer have a higher melt point than the film, thus the heat from the lands does not affect them. The heated lands 21 come into contact with the surface of the top fibrous web layer 14, but do not penetrate beyond that point. The heated lands 21 are therefore in a non-contact relationship with the film 12. As a result of securing in this manner, the present invention composite has three layers, an inner layer of a film 12 which has apertures, and the other two fibrous layers 14 and 16, as illustrated in FIG. 3, and FIG. 3A, which do not contain apertures. The shape and size of the apertures in the film may vary depending upon the application of the substrate, but the film should have an open area of at least 1% of the total surface area of the film. The open area being defined as the area of the apertures. The preferred apertured area is 45% of said surface area. The apertures may cover a majority of the surface of the film or they may be positioned in zones depending on the requirements of the product on which the present invention is used. In addition, because the top and bottom fibrous webs are not apertured, a matrix of fibers exist on each side of the apertures 24 as shown in FIG. 3, thus providing an additional barrier to fluid that has penetrated through the layers into an absorbent pad. This barrier aids in restricting the fluid to the pad. Although the hydrophobic top layer is the layer preferred to come into contact with the heated raised lands of the roll, the same results will occur if the hydrophilic bottom layer 16 is positoned so. The inner film 12 thickness should be at least 0.1 mil in order to cover the fibrous surface. Even though at least 0.1 mil is preferred, the thickness of the inner film 12 may range between 0.1 to 15 mils. Although it is preferred to use film that has been extruded and cured, freshly extruded film, still in a heat softened tacky state, may be placed directly on the fibrous web, thus enhancing and improving the securing of the film to the web. The fibrous layer(s) may be made from many different fiber types and quantities depending on the end use. It is preferred to utilize synthetic and natural hydrophillic (bottom) and hydrophobic (top) fibers in order to minimize the fluid holding capacity of the substrate. The weight of the fibrous web may vary between 4 to 100 grams per square yard (gsy) depending on the product design. The thickness of the layers together may vary depending on the required physical properties, such as machine and cross direction tensile strengths, fluid holding capacity, liquid penetration, etc. The three layers, as shown in FIG. 3, may be secured together with the fibers having varying degrees of fiber to film bonding, depending on the pressure and temperature used in the process.

Surface treatment/embossing is important and may be any continuous or discrete patterns with varied dimensions. The preferred method of aperturing is by the technique described in U.S. Pat. No. 3,507,943, of common assignee, incorporated by reference herein and which discloses the use of grooved rolls for bonding and aperturing. However, other methods, such as the use of engraved male and female rolls, engraved and smooth rolls, or endless belts may also be used. In the case of endless belts, hot air and a vacuum may be used to form the apertures and bond the layers. Another method of aperturing thermoplastic film is described in U.S. Pat. No. 3,038,198, of common assignee, also incorporated by reference herein.

The present invention as described herein is of particular advantage when used in disposable articles, such as sanitary napkins, because it will provide excellent softness, dryness, fluid penetration and other physical properties not available in prior art coversheets. When using the present invention coversheet on disposable articles, especially a sanitary napkin, which has an inner absorbent core or pad, the strike-through values or fluid penetration rate may be controlled without the need to attach the present invention coversheet onto the absorbent pad as is done in prior art. The term "strike-through" is defined as the time it takes a given amount of liquid to pass through a coversheet into an absorbent material. The less time it takes for the liquid to pass through the coversheet the better the strike-through value. To improve strike-through values, prior art disposable articles, such as sanitary napkins, have an adhesive layer, which totally covers the coversheet, and is between the coversheet and the absorbent pad layer. This additional layer was to insure good contact between the coversheet and the absorbent material. This contact is necessary because the fibers of the absorbent pad have to be as close as possible to the coversheet in order to wick fluid, that is on the coversheet, through it. No intermediate layer is necessary in the present invention substrate, because the bottom fibrous layer described herein is an integral part of the coversheet, therefore no closer contact can exit between a coversheet and an absorbent material. Furthermore, the hydrophobic fibrous layer next to the film does an excellent job of wicking any fluid through the top hydrophobic fibrous layer and film layer into it. The fluid is then transferred, by wicking, from the hydrophilic bottom fibrous layer into a hydrophilic absorbent pad. The excellent transfer of the fluid away from the top hydrophobic fibers which come into contact with the wearer's skin, keeps the top layer dry and therefore adds to the wearer's comfort. The aforementioned are significant advances and definite advantages over the prior art. Also, by varying the amount of hydrophilic fibers in the fibrous webs, the strike-through value of the present invention may be controlled, and the substrate may have varying degrees of fluid penetration, by the choice of the fibers used in the fibrous layers. For example, a mixture of hydrophilic and hydrophobic fibers, such as acrylic and polypropylene fibers, or cotton and polypropylene fibers. Thus, there is minimal fluid retained in the coverstock substrate of this invention. Another advantage of the present invention, which is due to the fact that the film of the present invention is apertured without penetrating the adjacent web. Thus, the web layers having no apertures, and when secured to the film, act as buffers between the film layer and absorbent pad, and film and skin of the wearer. This prevents particles of absorbent material from penetrating through the substrate to come into contact with the skin of the wearer. Because the webs are constructed of fibers their surfaces have a tendency to be fuzzy. This surface fuzziness gives an additional advantage to the present invention, in that the fuzzy surface of the bottom layer attaches very easily to other fibrous surfaces, such as an absorbent pad, thus securing the pad and coversheet together, eliminating any shifting of the absorbent pad within the sanitary napkin, when being worn. In addition, the surface of the top layer having a fuzzy surface is very soft and spongy, thus being very comfortable when placed against the skin of the wearer. The coversheet therefore is more stable on an absorbent pad, resulting in comfort and good pad stability. Still another advantage that the present invention has is the reduction of rewet or the dryness of the surface of coversheets in products using this invention. Rewet and dryness, for the purpose of this specification, are synonymous. Rewet may be defined as the amount of fluid, which will tend to flow from an absorbent pad back towards the outer face of the coversheet, when the pad is completely saturated. Thus, the less fluid to reach the surface of the coversheet, the dryer that surface remains. The present invention reduces rewet in two ways. First, by the hyrophilic fibrous layer slowing down the movement of the fluid by re-absorbing the fluid from the absorbent pad as the fluid moves outward from the pad. Secondly, when the fluid has moved through the fibrous layer, it comes in contact with the hydrophobic film layer and because of the resulting surface tension of the fluid with the film, a substantial amount of fluid will not pass outward through the apertures in the film, thus keeping the top layer of the fibrous web dry.

The present invention substrate will have a woven appearing surface, due to the affect of the embossing roll on the fibrous webs. In addition, the fibrous webs when secured or bonded to the film will provide support to the film. The substrate will also provide softness, comfort, and a cushioning effect due to the fibrous webs. The present invention substrate will have a textile appearance due to the apertures and the many different shapes, depth, etc. of micro embossing on the film surface, that may be used. For example, the embossed pattern may be pointed, circular, lines, etc. Also, by varying the percent open area of the apertures in the film, the ratio of strike-through to dryness may be changed. However, the more apertures in the film, which does give a better strike through, the greater the chance of rewet and wetting occurring in the coversheet, which is a definite disadvantage. Thus the preferred apertured area is 45% of the surface area. The optimum condition, as used in the present invention, is to have a sufficient amount of apertures in the coversheet as to give good fluid penetration or strike-through, while retaining the dryness on the coversheet outer surface which is against the wearer's skin. An important property of this present invention substrate is that the substrate may have varying degrees of dryness by using appropriate fibrous layers and film thickness.

The present invention also has excellent tensile strength, which is due to the fact that it has a plastic film incorporated within it.

To illustrate that the present embodiment has either superior or substantially equal properties to that of the prior art, a comparison test, to compare strike-through and rewet values of different coversheets was conducted. Two identical hygienic sanitary napkins, manufactured by Proctor and Gamble under the Trade name "Always" were used herein for comparison purposes. The coversheet of the Proctor and Gamble napkin is attached to the absorbent material, in the napkin, by hydrogen bonding. To make the comparison test one napkin, hereinafter referred to as "A", was tested with the coversheet as manufactured by Proctor and Gamble, while the other napkin, hereinafter referred to as "SAMPLE", had the coversheet carefully removed and the present invention substrate put in its place, as the coversheet. This was to insure that the same materials were used, with the exception of the coversheets. The strike-through values were arrived at by first subjecting "A", which had its original coversheet, to the following: 15.0 ml of fluid was deposited onto the coversheet of the napkin. The time it took for the fluid to pass through the coversheet into the absorbent portion of the napkin was measured. The strike-through time was then recorded. The "SAMPLE", with the present invention coversheet in place, was subjected to the same test with the strike-through time also being recorded. It should be noted that the strike-through values of both samples tested were within values acceptable to the consumer.

The rewet test, consisted of taking the wetted sanitary napkins, placing filter paper on the top of the coversheets and then placing a 5.0 pound weight on top of each of the filter papers. Prior to placing the filter paper on the napkins it was weighed. The weight compressed the napkin and forced some of the fluid to exit the napkin and be absorbed by the filter paper. The weight was left on each napkin for two (2) minutes. The weight and filter paper were then removed. The filter paper was then weighed, with the weight of each being recorded. The differences between the original weight and final weight were then determined.

The following are the results of that comparison test.

| PROPERTIES | TEST RESULTS | |
|---|---|---|
| | "A" | "SAMPLE" |
| Thickness (mils) | 15.5 | 12.0 |
| Strike-Through (sec) (coversheet) | 3.9 | 4.8 |
| Rewet (g) (dryness of the surface of coversheet) | 0.042 | 0.026 |

From the above results it should be noted that the "SAMPLE" coversheet proved to be approximately 50% dryer than "A", while having only 9 tenths of a second higher strike-through value. This is a substantial improvement over the dryness of prior art. The dryness of a coversheet is an important property, because it is of paramount importance with women in a sanitary napkin, to insure comfort. The present invention, as shown by the test results, exhibits a lower dryness factor than the prior art, thus a superior quality, and a substantial advantage over prior art.

The present embodiment, not only exhibits superior quality over prior art, but is also economical to make, because it is made in one process step, and is more comfortable.

It is not the intention of this specification to limit the present invention except to the following claims.

What is claimed is:

1. A composite substrate for use as a coversheet for disposable articles comprising:
   a top layer of hydrophobic fibrous web;
   a middle layer of thermoplastic film having heat embossed apertures therein; and
   a bottom hydrophilic fibrous web; said middle layer disposed in a surface to surface relationship with the inner surfaces of said top and bottom fibrous layers, said film and fibrous layers being secured together at least at the peripheral edges of said heat embossed apertures.

2. The coversheet of claim 1 wherein the nonwoven fibrous web may consist of synthetic or natural fibers or any combinations thereof.

3. The coversheet of claim 1 wherein the thickness of said thermoplastic film is at least 0.1 mil.

4. The coversheet of claim 1 wherein the open area of said coversheet is at least 1%.

5. The coversheet of claim 1 wherein the thermoplastic film is in a heat softened state.

6. The coversheet of claim 1 wherein apertures may cover a majority of the surface of said film or may be positioned in zones.

7. The coversheet of claim 1 wherein apertured area of said coversheet comprises a range of 1% to is 45%.

8. The coversheet of claim 1 wherein the bottom fibrous web has at least 5% hydrophobic fibers.

9. The coversheet of claim 1 where the top layer has at least 1% hydrophilic fibers.

10. The method of making coversheet for disposable articles of claim 1, comprising the steps of:
    providing a top layer of hydrophobic fibers;
    providing an intermediate layer of thermoplastic film;
    providing a bottom layer of hydrophilic fibers; and
    passing said layers between a pair of heated nip rolls, at least one of said nip rolls having a plurality of lands on its outer most surface.

11. The method of making a coversheet for disposable articles as recited in claim 10, including;
    heating said rolls;
    bringing said heated rolls into a close but non-contact relationship with said intermediate layer of thermoplastic film; and
    aperturing the intermediate layer of film by the radiation of heat from said lands on the outer most surface of said roll.

* * * * *